(12) United States Patent
Edgar

(10) Patent No.: US 9,020,184 B2
(45) Date of Patent: Apr. 28, 2015

(54) APPARATUS AND METHOD FOR RAPID AND PRECISE APPLICATION OF COSMETICS

(71) Applicant: TCMS Transparent Beauty LLC, Austin, TX (US)

(72) Inventor: Albert D. Edgar, Austin, TX (US)

(73) Assignee: TCMS Transparent Beauty LLC, Austin, TX (US)

( * ) Notice: Subject to any disclaimer, the term of this patent is extended or adjusted under 35 U.S.C. 154(b) by 109 days.

(21) Appl. No.: 13/946,170

(22) Filed: Jul. 19, 2013

(65) Prior Publication Data

US 2013/0302078 A1 Nov. 14, 2013

Related U.S. Application Data

(63) Continuation of application No. PCT/US2012/022296, filed on Jan. 24, 2012.

(60) Provisional application No. 61/435,644, filed on Jan. 24, 2011, provisional application No. 61/435,627, filed on Jan. 24, 2011, provisional application No. 61/435,604, filed on Jan. 24, 2011.

(51) Int. Cl.
| | |
|---|---|
| *G06K 9/00* | (2006.01) |
| *A45D 34/00* | (2006.01) |
| *A45D 44/00* | (2006.01) |
| *A61B 5/103* | (2006.01) |
| *A61B 5/00* | (2006.01) |
| *G09B 19/00* | (2006.01) |

(52) U.S. Cl.
CPC .............. *A45D 34/00* (2013.01); *A45D 44/005* (2013.01); *A45D 2044/007* (2013.01); *A61B 5/103* (2013.01); *A61B 5/441* (2013.01); *A61B 5/448* (2013.01); *A61B 5/449* (2013.01)

(58) Field of Classification Search
CPC .................................. G06K 9/00; G09B 19/00
USPC ......... 382/100, 103, 106, 108, 118, 121–123, 382/128, 140, 162, 167–168, 173, 181, 199, 382/210, 219, 232, 254, 274–276, 305, 312, 382/321; 132/200; 434/100, 102; 348/207.1
See application file for complete search history.

(56) References Cited

U.S. PATENT DOCUMENTS

| | | | |
|---|---|---|---|
| 5,985,252 A | 11/1999 | Hall et al. | |
| 7,648,364 B2 * | 1/2010 | Dauga et al. ................... | 434/100 |
| 8,695,610 B2 * | 4/2014 | Samain et al. ................. | 132/200 |
| 2007/0110305 A1 * | 5/2007 | Corcoran et al. .............. | 382/167 |
| 2008/0192999 A1 * | 8/2008 | Edgar et al. .................... | 382/128 |
| 2010/0214421 A1 * | 8/2010 | Qu et al. ....................... | 348/207.1 |

\* cited by examiner

OTHER PUBLICATIONS

International Preliminary Report on Patentability, International Application No. PCT/US2012/022296 mailed Aug. 8, 2013, 8 pages.

*Primary Examiner* — Seyed Azarian
(74) *Attorney, Agent, or Firm* — Fish & Richardson P.C.

(57) ABSTRACT

A method for selectively applying a reflectance modifying agent (RMA) to an area of skin, the method comprising receiving an image of the area of skin, identifying, using the image, a nominated point within the area of skin, determining an actual reflectance of the nominated point, applying an edge protection technique based on the image to generate one or more outputs, determining a desired reflectance of the nominated point based on the one or more outputs, calculating an amount of RMA to be applied based on the output, and determining whether to apply the RMA to the area of skin based on the amount of RMA.

18 Claims, 4 Drawing Sheets

APPARATUS AND METHOD FOR RAPID AND PRECISE APPLICATION OF COSMETICS

CROSS-REFERENCE TO PRIOR APPLICATION

This is a continuation of International Patent Application No. PCT/US2012/022296, filed Jan. 24, 2012 and entitled "Apparatus and Method for Rapid and Precise Application of Cosmetics," which claims priority to U.S. Provisional Patent Applications No. 61/435,604 filed Jan. 24, 2011, No. 61/435,627 filed Jan. 24, 2011, and No. 61/435,644 filed Jan. 24, 2011, the subject matter of all of which is incorporated herein by reference in its entirety.

BACKGROUND

Manual cosmetic applications are imprecise compared to computer-controlled techniques, and this imprecision may make them less effective. For example, the heavy application of a foundation base for makeup may cause an unattractive, caked-on appearance. The selective, precise application of reflectance modifying agents (RMAs) through computer-controlled techniques can provide a more effective, more automated, and less expensive modification of the appearance of skin.

There is a need to make such computer-controlled techniques fast and, precise, and well able to create desired effects, especially for a device moved by a user in a random direction.

SUMMARY

Implementations of the present disclosure include methods of for selectively applying a reflectance modifying agent (RMA) to an area of skin. In some implementations, methods include receiving an image of the area of skin, identifying, using the image, a nominated point within the area of skin, determining an actual reflectance of the nominated point, applying an edge protection technique based on the image to generate one or more outputs, determining a desired reflectance of the nominated point based on the one or more outputs, calculating an amount of RMA to be applied based on the output, and determining whether to apply the RMA to the area of skin based on the amount of RMA.

In some implementations, applying an edge protection technique includes generating a filtered image based on the image, and comparing the filtered image to the image to provide an output of the one or more outputs. In some implementations, methods further include determining that the image is lighter than the filtered image based on the comparing, and providing the image as the output. In some implementations, methods further include determining that the filtered image is lighter than the image based on the comparing, and providing the filtered image as the output.

In some implementations, applying an edge protection technique includes defining a protection area that is larger than the nominated point and that encompasses the nominated point, identifying a peak reflectance within the protection area, and generating an output of the one or more outputs based on the peak reflectance and the actual reflectance. In some implementations, the output comprises a corrected actual reflectance. In some implementations, the corrected actual reflectance is calculated based on the following equation: $R_{SKINCORR} = R_{SKIN} + K(R_{SKIN} - R_{PEAK})$; where $R_{SKINCORR}$ is the corrected actual reflectance, $R_{SKIN}$ is the actual reflectance, $R_{PEAK}$ is the peak reflectance and K is a gain. In some implementations, the peak reflectance is a minimum reflectance. In some implementations, the peak reflectance is a maximum reflectance.

In some implementations, methods further include calculating a target opacity based on the desired reflectance, the output and a reflectance of the RMA, wherein the amount of RMA is determined based on the target opacity. In some implementations, the amount of RMA is determined from a look-up table using the target opacity as an input.

In some implementations, methods include generating an image of the area of skin, identifying, using the image, a nominated point within the area of skin, determining an actual reflectance of the nominated point, applying a rapid median filter to determine a desired reflectance of the nominated point, calculating an amount of RMA to be applied based on the actual reflectance and the desired reflectance, and determining whether to apply the RMA to the area of skin based on the amount of RMA.

In some implementations, applying a rapid median filter comprises calculating a rapid median average for an area of interest, the area of interest encompassing the nominated point. In some implementations, the area of interest includes a shape having a center that is coincident with a center of the nominated point. The shape is a circle. The shape is a square. The shape is a square. In some implementations, the rapid median average is calculated over pixels surrounding the nominated point. In some implementations, the rapid median average is calculated for a single pixel centered over an area immediately below a deposition nozzle.

In some implementations, methods include generating an image of the area of skin, identifying, using the image, a nominated point within the area of skin, determining an actual reflectance of the nominated point, determining a desired reflectance of the nominated point, and calculating an amount of RMA to be applied based on the actual reflectance and the desired reflectance, the RMA comprising an opacity ranging between 1% and 40%, an average particle size ranging between 1 and 30 microns, a volatile carrier comprising one or more alcohols ranging between 12.0% and 68.5% by weight.

In some implementations, the RMA comprises an opacity ranging between 2% and 20%.

In some implementations, the RMA comprises an opacity ranging between 5% and 15%.

In some implementations, the RMA comprises an average particle size ranging between 1 and 10 microns.

In some implementations, the RMA comprises an average particle size ranging between 3 and 5 microns.

In some implementations, the volatile carrier includes one or more alcohols ranging between 62.0% and 68.5% by weight.

In some implementations, the volatile carrier includes one or more alcohols ranging between 66.6% and 67.8% by weight.

In some implementations, the RMA includes a viscosity ranging between 42 and 44 centipoise (cps).

The present disclosure also provides a computer-readable storage medium coupled to one or more processors and having instructions stored thereon which, when executed by the one or more processors, cause the one or more processors to perform operations in accordance with implementations of the methods provided herein.

The present disclosure further provides handheld devices for implementing the methods provided herein.

It is appreciated that methods in accordance with the present disclosure can include any combination of the aspects and features described herein. That is to say that methods in accordance with the present disclosure are not limited to the combinations of aspects and features specifically described herein, but also include any combination of the aspects and features provided.

The details of one or more embodiments of the present disclosure are set forth in the accompanying drawings and the description below. Other features and advantages of the present disclosure will be apparent from the description and drawings, and from the claims.

DESCRIPTION OF DRAWINGS

Like reference symbols in the various drawings indicate like elements.

DETAILED DESCRIPTION

Figure 1:
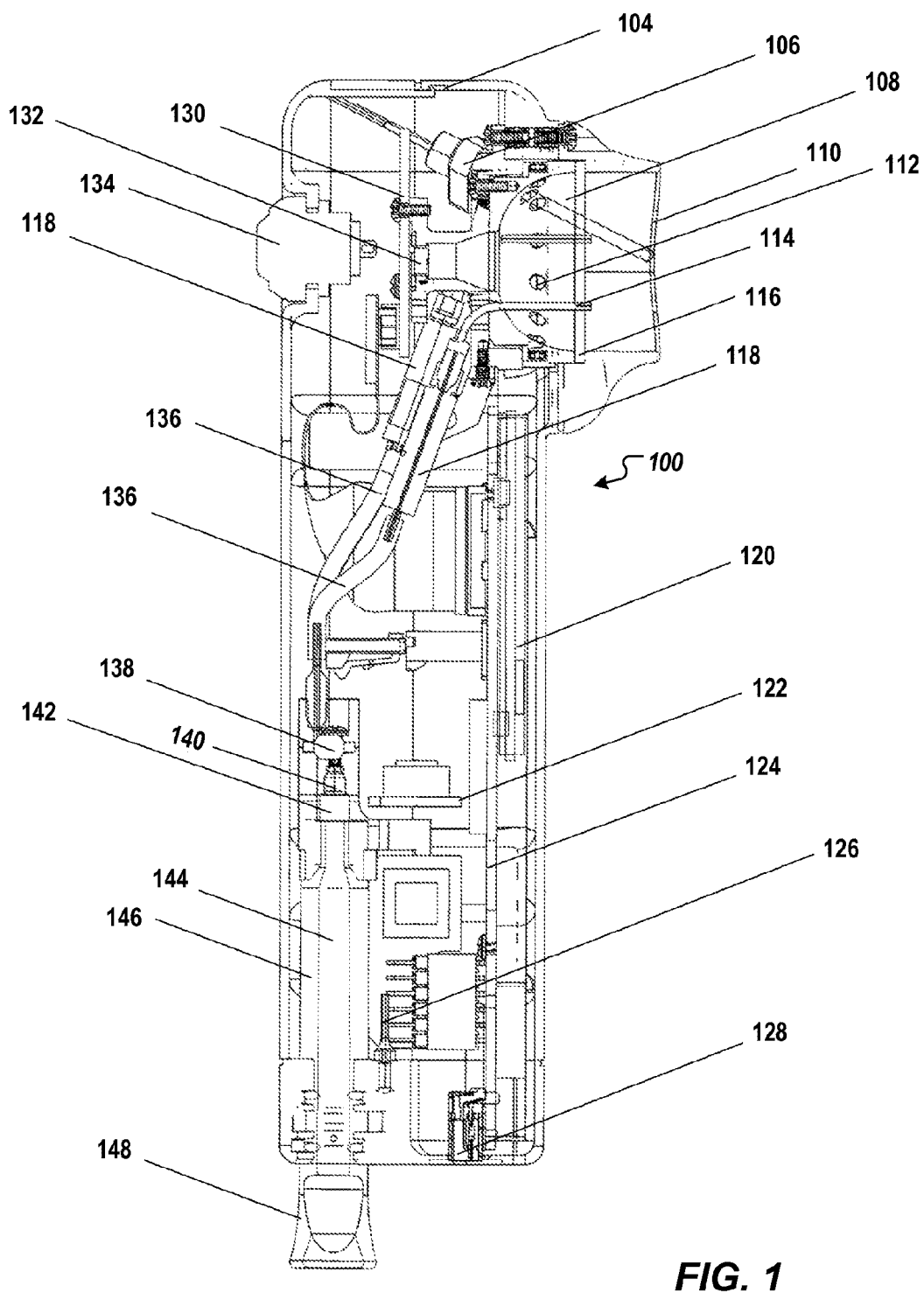
FIG. 1 is a representative diagram that illustrates a cross-sectional view of an example handheld applicator device.

Implementations of the present disclosure generally build on apparatus and methods disclosed in each of U.S. patent application Ser. No. 11/503,806 (US20070035815), entitled "System and Method for Applying a Reflectance Modifying Agent to Improve the Visual Attractiveness of Human Skin," and filed on Aug. 14, 2006, U.S. patent application Ser. No. 12/029,524 (US20080194971), entitled "System and Method for Applying a Reflectance Modifying Agent Electrostatically to Improve the Visual Attractiveness of Human Skin," and filed on Feb. 12, 2008, U.S. patent application Ser. No. 12/028,836 (US20080219528), entitled "System and Method for Providing Simulated Images through Cosmetic Monitoring," and filed on Feb. 11, 2008, U.S. patent application Ser. No. 12/028,835 (US20080193195), entitled "Handheld Apparatus and Method for the Automated Application of Cosmetics and Other Substances," and filed on May Feb. 11, 2008, U.S. patent application Ser. No. 12/029,534 (US20080192999), entitled "System and Method for Applying a Reflectance Modifying Agent to Change a Person's Appearance Based on a Digital Image," and filed on Feb. 12, 2008, and U.S. patent application Ser. No. 12/129,624 (US20090025747), entitled "Apparatus and Method for the Precision Application of Cosmetics," and filed May 29, 2008. The disclosures of the above-identified patent applications are expressly incorporated herein by reference in their entireties.

In the present disclosure, the term reflectance modifying agent (RMA) refers to any compound useful for altering the reflectance of skin. Examples RMAs can include cosmetics, inks, dyes, pigments, bleaching agents, chemically altering agents, and other substances that can alter the reflectance of human skin and other features. An RMA composition is a composition that includes at least one RMA. An RMA composition can include other ingredients such as a moisturizer, a carrier, or an active ingredient such as a beneficial compound. A transparent RMA can be provided as a dye, although dilute pigmented RMAs are essentially transparent also. An opaque RMA can include high refractive index particles. In one example of pigmented cosmetics, the term "high refractive index particles" refers to particles having a refractive index of 2.0 or greater.

The term frexel is defined as a small pixel-like region of the skin, which may represent a single large pixel or a small number of pixels. More specifically, a pixel refers to the area of the deposition on a surface immediately below the deposition aperture of a cosmetic applicator, for example, an electrostatic airbrush applicator. For some embodiments, a pixel may represent an area of $\frac{1}{15}$" to $\frac{1}{5}$".

The term skin is used not only to refer to skin as on the surface of the human body, but also to refer more broadly to any human feature that may be enhanced cosmetically, for example, fingernails, hair, and other keratinaceous surfaces. The term skin includes, but is not limited to, areas of human skin including the face, head, neck, torso, back, legs, arms, hands, and feet.

The term attribute means the local reflectance of skin, the surface morphology of the skin, or both. The term attribute is a subset of the broader term characteristic, which refers to any measurable skin property. The terms "in register in agreement" or "in agreement" mean specifically applying an RMA in register to frexel attributes in a manner to accentuate one or more frexels of a feature such as applying a light RMA to lighten a light skin feature; applying a dark RMA to darken a dark feature; adding red RMA to a red frexel; and applying RMA to a dimple to highlight the dimple. The terms "in register in opposition" or "in opposition" mean specifically applying an RMA in register to frexel attributes in a manner to conceal or cover one or more frexels of a feature such as applying a light RMA to a dark skin feature to lighten the feature; applying a dark RMA to a light feature to darken the skin; adding a green or blue RMA to a red frexel; and applying a light RMA to a portion of a wrinkle to hide the wrinkle.

The term "middle spatial frequencies" means features or frequencies in the approximate range of 1.5 to 8 mm on a face and 2-16 mm on a leg. In the spatial frequencies between 2 mm to 12 mm, weaker waves below for example 10% peak to peak reflection can be attenuated, but stronger waves can be retained. In the range 0.5 to 2 mm, the same can be done with a higher threshold, below 0.5 mm the spatial frequency waves can be retained. In the range 12 to 25 mm, the same threshold can be applied under restricted control. Filtering or partial camouflaging of middle spatial frequencies means selectively applying RMA in a manner to disguise or cover middle spatial frequency features such as age spots.

The term "differentiated RMA" means an RMA that is deliberately selected to be darker (have less luminance) or lighter (have more luminance) than a desired skin color.

The term "highly differentiated RMA" means an RMA that is deliberately selected to be substantially darker or lighter than a desired skin color. Technically, a highly differentiated RMA is typically at least 85% saturated in the red channel and is selected along an extension of the vector between the actual local skin reflectance and the desired skin reflectance. In the example of lightening a dark feature, a highly differentiated RMA might look pink. The term "skin color" means the skin's hue, chroma, and luminance. Perceived skin color is influenced by factors such as the actual skin color, lighting, and texture.

The term "opacity" means the amount of coverage that the RMA provides over the substrate surface. There are two extremes. If a cosmetic is 100% opaque, a viewer would see the pure bulk color of the cosmetic. If a cosmetic is perfectly transparent, that is 0% opaque, a viewer would see the pure skin color under the cosmetic. If a cosmetic is 50% opaque, a viewer would see a 50-50 average of the cosmetic and skin color.

The phrase "eraser-like movement" refers to a general back-and-forth, circular, or generally elliptical motion. The motion is similar in concept to using a pencil eraser to erase a word on a sheet of paper. The term illuminator refers to a light source that is used to illuminate a portion of a surface. Illuminators are typically controllable so that data from various lighting arrangements can be used to correct for ambient light and to obtain accurate reflectance or surface profile data. Illumination states or illumination conditions refers to various combinations of a plurality of sensors in ON or OFF states. The term LED refers specifically to a light emitting diode, and more generally to an example of an illuminator.

The term sensor refers to a photodiode, phototransistor, or other optical detector. In some embodiments, a camera functions as one or more sensors. The housing may be shapes other than annular.

A "deposition device" is a device that applies an RMA to the skin. In this specification, the deposition device may be a sprayer, including an electrostatic sprayer or airbrush sprayer, a drop control device, or other apparatus. A "deposition element" is a portion of a deposition device that applies an RMA, such as a sprayer, a drop control element, or both. A "scanning and deposition device" scans a portion of the skin and uses scan data to control a deposition of one or more RMA. An example of a drop control element is an inkjet print head where individual droplets are precisely controlled. An example of a non-drop control element is a sprayer. Spray devices are non-drop control techniques where droplets are produced and controlled only in aggregate.

The term reflectance is the ratio, provided as a percentage, of light reflected from a surface to the light impinging on the surface. The terms optical density, or density can refer to a measure of the reflection of the skin. In this specification, an "initial reflectance" reading is an initial reflectance reading from a sensor, before compensating for distance or tilt. An "adjusted reflectance" reading compensates the initial reflectance reading for distance and tilt of a surface from a sensor ring. Adjusted reflectance is a reflectance reading corrected for device height and tilt relative to the skin surface. A "desired density level" is typically a desired level of smoothing for an area of skin, such as threshold for lightening skin, darkening skin, or both. An "average density" over an area of skin may be used as the desired density level. The term "RMA application density" refers to the mass per unit area of RMA applied to a surface.

The term handheld includes devices that are self-contained in a housing that may be held in a hand as well as devices where a housing is tethered to power supply and/or computer.

Implementations of the present disclosure are generally directed to apparatus and methods for rapid and precise application of reflectance modifying agents (RMAs), including cosmetics, to skin. Implementations of the present disclosure provide control of a handheld deposition device to rapidly apply relatively small amounts of an RMA in register with measured skin attributes. In some implementations, one or more sensors, such as one or more cameras, and an image processing system view an area of skin. A processor activates a deposition system to apply one or more RMAs a location known to the processor relative to an image of the skin.

As discussed in further detail herein, deposition devices in accordance with implementations of the present disclosure can include at least one deposition element that is controlled by a processor. The processor processes data obtained from one or more sensors that are responsive to light reflected from the skin. Each of the one or more sensors can include a sensor that is sensitive to the amount of reflected light in one or more wavelengths. Example sensors can include, but are not limited to, one or more cameras, one or more photodiodes and/or one or more phototransistors. One or more illuminators, also termed light sources, can be provided. Each light source can include a light emitting diode (LED). In some implementations, the multiple light sources are turned on simultaneously in order to provide a uniform lighting for an area of skin. In this manner, reflectance can be accurately measured with sufficient illumination to permit the use of a polarizing filter. The use of multiple light sources provides additional flexibility to sequence the light sources to provide different lighting states. In this manner, data indicative of skin topology can be obtained. The use of multiple light sources also enables a pairing of one or more light sources with one or more photodiodes, for example. In some implementations, a single light source, such as a ring light, can be provided.

In some implementations, conventional cosmetic application devices are adapted to provide scanning and control capability. Example conventional cosmetic application devices can include an airbrush or electrostatic spray device. Such devices can be adapted by modifying the deposition strategy from large-scale uniformity to more precise, selective deposition that can include multi-pass deposition. The deposition strategy may also use more extreme colors, rather than a base color that is selected to be close to the skin color. The device may deposit a wide range of RMAs under precise computer-control. In some examples, the RMA may be much darker or lighter than the skin, and the RMA may be applied lightly to the skin in multiple passes.

Implementations of the present disclosure include using motion for scanning, and deposition. In particular, a user of the handheld deposition device moves the deposition device manually across an area of skin. The movement can correspond to the familiar and instinctive pattern of moving an eraser. As the handheld deposition device is caused to move over the area of skin, the deposition device scans a plurality of frexels. The deposition device automatically deposits one or more RMAs in response to the reflectance attributes of the frexels to improve the appearance of the area of skin Movement of the deposition device can include any pattern or combination of patterns. Example patterns can include along a row in one direction, followed by an application in another area to let the RMA dry on the first row.

Implementations of the present disclosure include the use of multiple deposition heads. In particular, the use of multiple deposition heads can increase the speed and effectiveness of sensing, analysis and deposition. For most users, the handheld deposition device is most freely usable, if it is directionally agnostic. The use of multiple deposition heads enables the deposition device to be directionally agnostic. In some implementations, the multiple deposition heads can be arranged in a non-linear pattern. For example, multiple deposition heads arranged in a linear pattern provides two "ideal" directions of motion (e.g., forward and backward along a linear axis running through the two deposition heads). A triangle arrangement of three deposition heads within a generally circular pattern provides six "ideal" directions of motion as opposed to two "ideal" directions of motion for three heads arranged in a line. With a large number of deposition heads, arrangement in a pure circle may provide excessive overlap of head trajectories on the edge of the circle parallel to the direction of motion. A uniform density across an area, such as the area enclosed by a circle, can provide a more uniform coverage in all directions as the handheld device is moved.

Figure 2:
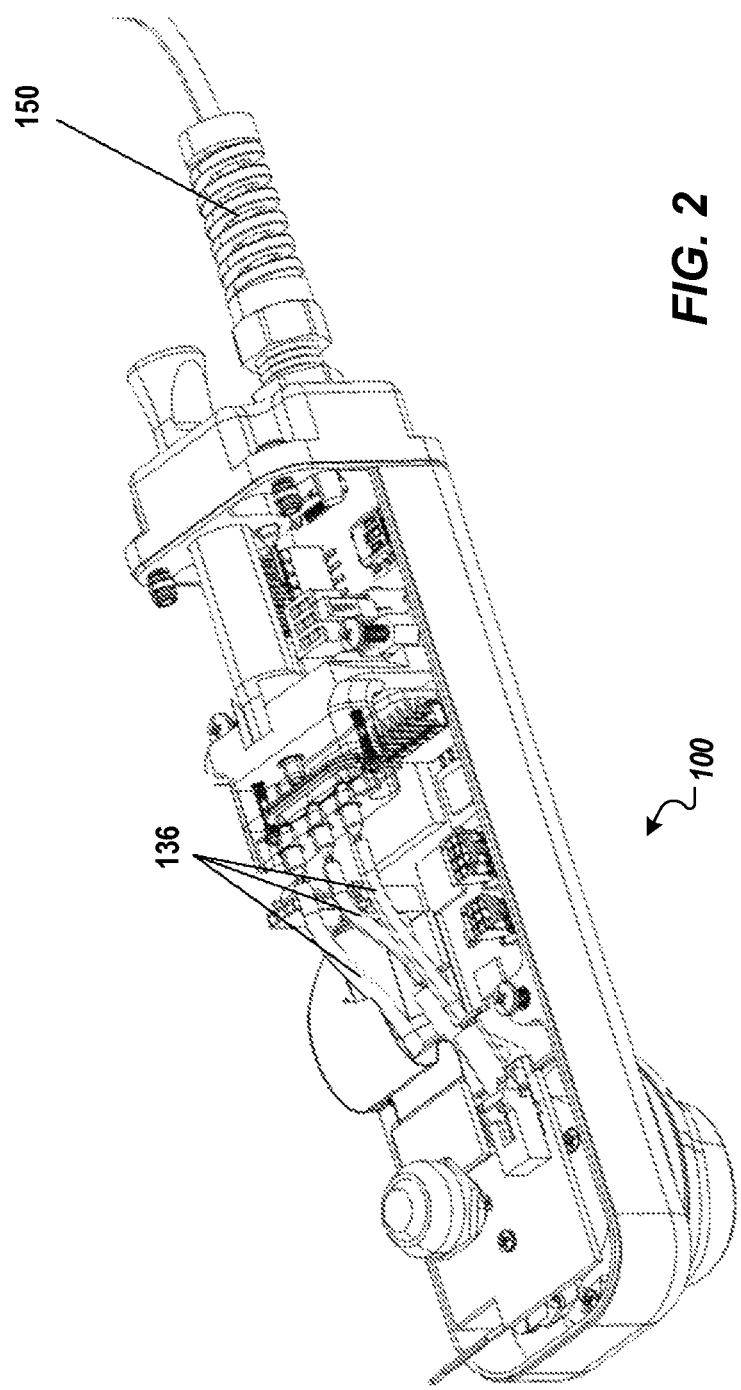
FIG. 2 is a representative diagram that illustrates a top perspective view of a computerized applicator.
Figure 3:
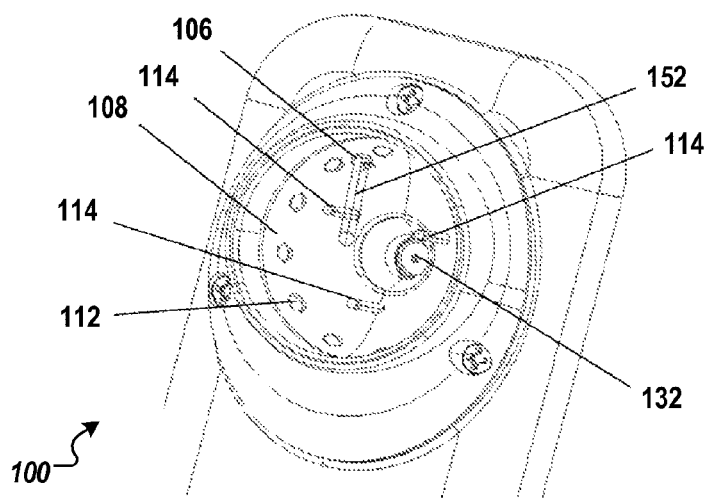
FIG. 3 is a representative diagram that illustrates a side perspective view of deposition, lighting, and sensing elements in the top of a computerized applicator.

Referring now to FIGS. 1-4 an example handheld applicator device 100 will be discussed in detail. FIG. 1 illustrates a cross-sectional view of the example handheld applicator device 100. The applicator device 100 includes a case 104 that encloses and protects other components discussed herein. The case 104 can be manufactured out of plastics and/or other materials, and can be shaped or contoured to ergonomically accommodate a human hand grasping the applicator device 100. A fiducial source 106 generates a fiducial 152 (FIG. 3). The fiducial 152 can be used to automatically determine a distance between the applicator device 100 and skin to be treated. The fiducial 152 can also be used to determine a tilt of the applicator device 100 relative to the skin, as well as a morphology of the skin. In some implementations, the fiducial source 106 can include a focused LED that is used to generate the fiducial 152. In some implementations, the fiducial source 106 can include a laser. For example, the fiducial source 106 can include a 650 nm Class 1 red laser and/or a blue (e.g., 465 nm) LED. For example, if the sensor is an RGB camera, the red light is sensed only in the red channel or blue in the blue channel, which are easily distinguished from the skin image data in the green channel.

The applicator device 100 further includes an illumination dome 108. The illumination dome 108 provides a source of illumination that is small enough to fit into a handheld device and that can provide uniform distribution of light. The illumination dome 108 further enables an adequate intensity of the distributed light for sensing the skin to be treated. A spacer 110 is provided as a physical element that provides for the faster estimation by the user of a desired distance of the application device 100 from the skin for deposition. The spacer 110 can include a plastic cylinder. In some implementations, the spacer 110 can include raised elements on an outer edge to enable the applicator device 100 to glide easily over the skin. Example raised elements can include fibers and/or knobs. In some implementations, three raised knobs may be used in a triangular configuration that reduces blockage to sensing and deposition. In some implementations, an outer edge of the spacer 110 can be coated with a compound to make the gliding motion easier. An example compound can include silicon.

The applicator device 100 further includes one or more illuminators 112. In some implementations, the illuminators 112 are provided as one or more green LEDs. Green is a beneficial lighting color for collecting data about blemishes on skin. Further, green light can provide improved visibility of skin conditions relative to red or other wavelengths. In some implementations, the illuminators 112 includes LEDs positioned a short distance from a filter, discussed in further detail below, on the same side as a sensor, also discussed in further detail below. In this manner, the illuminators provide ample light for reflectance measurement. In some implementations, a high brightness of the LEDs permits the applicator device 100 to be effective in ambient lighting conditions.

The applicator device 100 further includes a nozzle 114. The nozzle 114 provides an outlet of the deposition system, and is used to jet one or more RMAs onto the surface to be treated. In some implementations, multiple nozzles 114 may be used to increase the speed of deposition. For example, three nozzles 114 can be provided. Each nozzle 114 can correspond to the same RMA (e.g., type and/or color), or can correspond to different RMAs (e.g., type and/or color). In some implementations, each 114 nozzle can be activated to deposit an RMA when a target area is directly underneath the particular nozzle 114, and can be activated independently of the other nozzles 114. A valve 118 is provided and can be regulated to control the flow of RMA through the deposition nozzle 114. In the case of multiple nozzles 114, multiple valves 118 can be provided, one valve 118 corresponding to each nozzle 114.

The applicator device 100 can further include a polarizing filter 116. The polarizing filter 116 is used to eliminate the effects of gloss, reflections from the skin thereby increasing the accuracy of brightness measurements of the skin. In some implementations, a circular polarizing filter 116 may be used.

The applicator device 100 further includes an image processing circuit board 120, and one or more accelerometers 122. Each of the one or more accelerometers 122 is sensitive to movement and orientation of the applicator device 100 and can generate a signal indicating, for example, the magnitude and direction of an acceleration of the applicator device 100, and can be used to sense orientation, acceleration, to enhance motion prediction, image processing and deposition decision-making processing. The applicator device 100 further includes a central-processing unit (CPU) board 124, a pressurized air connector 126, a video output 128, and a camera board 130 that is programmed to control the operation of at least one sensor camera (not shown). The applicator device 100 further includes a camera lens 132 that is used to focus the at least one sensor camera (not shown), a power switch 134 that is used to turn the applicator device on and off.

The applicator device 100 further includes a fluid manifold 138 and a tube 136 that fluidly connects the fluid manifold 138 to a corresponding valve 118. In some implementations, multiple tubes 136 are used to connect the fluid manifold 38 to multiple valves 118. One or more removable reservoirs 144 are provided. Each removable reservoir 144 can be provided as a cartridge that is defined by a reservoir barrel 146 ahf that contains an RMA. In some implementations, a single reservoir 144 is provided, such that the applicator device 100 deposits a single RMA (e.g., type and/or color). In some implementations, multiple reservoirs 144 are provided, such that the applicator device 100 deposits one or more different RMAs (e.g., type and/or color). A canula 140 is provided an pierces a septum 142 of a corresponding reservoir 144 when the reservoir 144 is inserted into the applicator device 100. The septum 142 retains the RMA within the reservoir 144. A reservoir handle 148 can be provided at the end of the reservoir 144, and can be used to insert or remove the reservoir 144 from the applicator device 100.

Referring now to FIG. 2, a perspective view of the applicator device 100 is illustrated with a portion of the case 104 removed. A applicator device 100 can include a supply conduit 150. The supply conduit 150 can be used to supply electrical power and/or pressurized fluid (e.g., air) to the applicator device 100 from respective external sources.

Referring now to FIG. 3, a perspective view of a head portion of the applicator device 100 is illustrated. In particular, FIG. 3 illustrates deposition, lighting and sensing components. The components illustrated in FIG. 3 include the fiducial source 106, the illumination dome 108, the at least one LED 112, the nozzles 114, and the camera lens 132. FIG. 3 also illustrates the fiducial 152 that is generated by the fiducial source 106.

Figure 4:
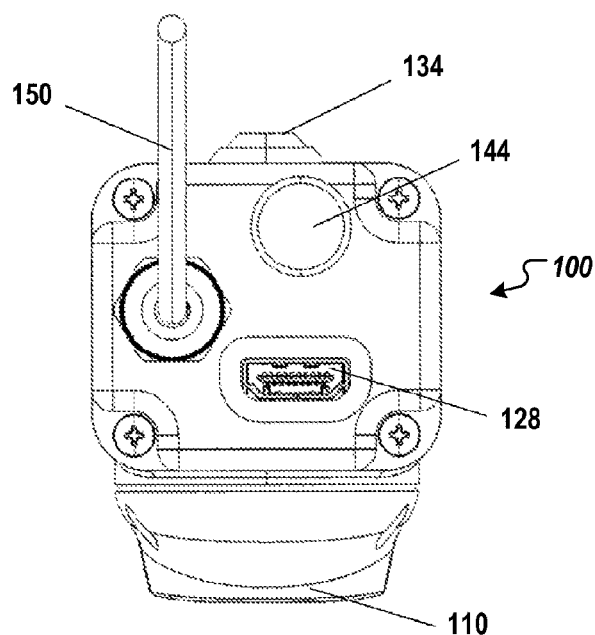
FIG. 4 is a representative diagram that illustrates a back perspective view of a computerized applicator.

Referring now to FIG. 4, an end view of the example applicator device 100 is illustrated. In particular, FIG. 4 depicts the spacer 110, the video output 128, the power switch 134, the reservoir 144, and the supply conduit 150.

Implementations of the present disclosure are further directed to methods for processing images, determining attributes, calculating enhancements, and activating deposition component. As discussed in further detail herein, methods of the present disclosure can be realized using digital electronic circuitry, or in computer hardware, firmware, software, or combinations thereof.

In some implementations scanned attributes of an area of skin or other feature are identified and the automatic and precise deposition of one or more RMAs can be initiated on the area. In some implementations, a deposition device, such as the applicator device 100 of FIGS. 1-4, is moved manually back and forth across the area in multiple passes, to continually scan and determine values of one or more attributes of the area relative to one or more threshold values. Example attributes can include lightness and darkness of the area of skin. The one or more threshold values can be set by means of the software and can correspond to a cosmetic improvement in the appearance of the area. In some implementations, the deposition device automatically deposits the one or more RMAs until the measured attribute values achieve the threshold value. For example, the deposition device can automatically deposit the one or more RMAs until the measured attribute values exceed or fall below the threshold value. In some implementations, the threshold value can correspond to a target value, where the deposition device automatically deposits the one or more RMAs until a difference between a measured attribute value and the threshold value falls below a threshold difference.

Different implementations may be used to treat a relatively large skin area such as a face, arm, and/or leg. Other implementations may be used to selectively treat only one or a few skin features of interest to the user without moving a scanning or deposition element over other areas of the skin.

In some implementations, the movement of the deposition device may be random in the sense that the processor may not have control over the location of the point of deposition. For example, a user may move the deposition device over the skin in random patterns. In other implementations, the deposition device may be in a fixed position, but the user may move relative to the deposition device in random patterns. For example, the deposition device may be installed in a booth.

The processor may be programmed to know at any time the location of an aim point of potential deposition if the processor gave the command to fire. In this case, the aim point is said to be "nominated" by the, in some ways, random motion of the hand. The processor has the choice of "electing" the nominated point by "firing," or otherwise applying the cosmetic at that point, or may choose to wait for the next nominated point based on the movement of the hand, over which the processor is aware but does not have direct control. This is referred to as the "random nomination" approach, as distinguished from a system in which the processor has the ability to aim a deposition directly at a defect that it chooses.

Figure 5:
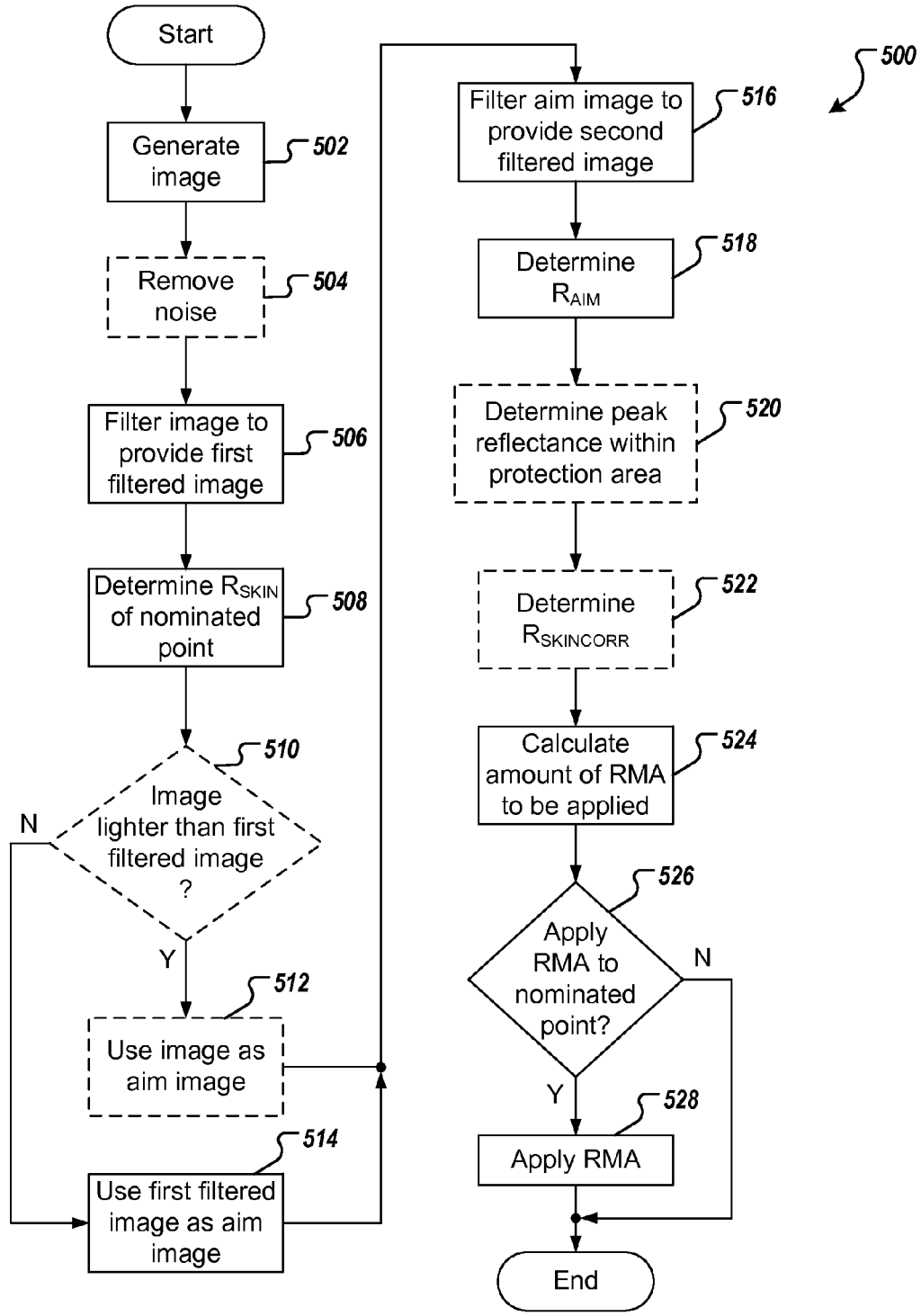
FIG. 5 is a chart that illustrates methods used for a deposition device that can be used for the rapid and effective application of RMAs.

FIG. 5 illustrates an example process 500 for a random nomination approach to calculate an amount of RMA (e.g., a cosmetic) to be applied to an area of skin. In general, the example process includes operations 502-528. Operations 504, 510, 512, 520 and 522 are illustrated using a dashed line to indicate that operations 504, 510, 512, 520 and 522 are optional. In particular, one or more of operations 504, 510, 512, 520 and 522 are directed to refinements of a general example process 500 and can be included in various implementations in accordance with the present disclosure.

In some implementations, the example process 500 includes the operations 502, 506, 508, 514, 516, 518, 524, 526 and 528. An image of the area of skin is generated (502). For example, the applicator device 100 of FIGS. 1-4 can be used to generate the image of the area of skin using a sensor (e.g., a camera) and the illuminators 112. The image is filtered to provide a first filtered image (506). For example, the CPU board 124 of the applicator device 100 can apply a low-pass filter to the image to remove frequencies that are greater than a first threshold. Consequently, the first filtered image only includes frequencies that are lower than the first threshold. In general, the filtering provides a simple averaging of color within the first image to provide the first filtered image.

The reflectance of a nominated point within the first filtered image is determined (508). The nominated point corresponds to an area of skin that is located below one or more of the nozzles 114 of the applicator device 100, and would be impacted by the application of an RMA. The calculated reflectance is referred to as $R_{SKIN}$. In some implementations, $R_{SKIN}$ is calculated by averaging the skin reflectance around the nominated point. The averaging covers an area and weight approximately matching the area to be covered by and affected by a dot of RMA that would be deposited. In some implementations, the skin reflectance of pixels of the outer edges of the area can be weighted relative to the skin reflectance of pixels toward or at the center of the area. Accordingly, $R_{SKIN}$ can be provided as the average color of the skin occupying the nominated point. The average can be determined based on the low-pass filtering, discussed above. In some implementations, the nominated point includes an example diameter of approximately $\frac{1}{15}$" (1.7 mm). In some implementations, a simple average is taken over a circular area with a diameter of $\frac{1}{15}$" (1.7 mm). In some implementations, the simple average can be taken over other shapes and weights, for example a square or a Gaussian shape. The first filtered image is used as the aim image (514) to determine the aim reflectance, as discussed in further detail herein.

The aim image is filtered to provide a second filtered image (516) and the aim reflectance is determined (518). The calculated aim reflectance is referred to as $R_{AIM}$. For example, the CPU board 124 of the applicator device 100 can apply a low-pass filter to the image to remove frequencies that are greater than a second threshold. Consequently, the second filtered image only includes frequencies that are lower than the second threshold. In general, the filtering provides a simple averaging of color within the aim image to provide the second filtered image. The second threshold can be lower than the first threshold. More generally, $R_{AIM}$ is determined as the average skin reflectance over a larger area around the nominated point within the aim image. This average can be provided as a median average to ignore small skin defects, such as hairs or freckles in the form of lines or dots. Correcting middle frequency skin patterns to the low frequency average skin color gives a desirable visible benefit. This difference between a large area average and a small area average extracts the middle spatial frequencies, providing a target to improve visual benefit.

In some implementations, a rapid median average can be calculated for an area of interest having an example diameter of approximately $\frac{2}{5}$" (10.16 mm), the center of which is coincident with the center of the nominated point. A rapid median average is performed only over the pixels surrounding a specific, nominated point to be treated, and only for the single pixel centered over the area immediately below a deposition nozzle. In some implementations, the median average may be taken for areas of interest represented by other shapes. For example, a square may be used, the center of which is coincident with the center of the nominated point. In some implementations, areas of interest with other diameters besides $\frac{2}{5}$" (10.16 mm) may be used. However, if an area of interest is too small, larger defects approaching the size of the area being averaged may not be corrected. On the other hand, if the diameter of the averaged area is too large, corrections may be made to large areas where corrections are undesirable, such as cheeks. The device may also become too expensive or bulky because hardware required for the field of view would become too large and expensive to be practical.

The amount of RMA (e.g., cosmetic) to be applied is calculated (524). For example, the amount of RMA can be determined by the CPU board 124 of the applicator device based on $R_{AIM}$ and $R_{SKIN}$. The amount of RMA corresponds to the amount needed to achieve $R_{AIM}$ at the nominated point. Assuming simple linear opacity characteristics of the RMA on skin, which is a good approximation of the optical properties for many pigmented cosmetics on skin, for example, a desired, or target opacity of the to be applied RMA can be calculated using the following formula for reflectance values:

$$\text{Target Opacity} = (R_{AIM} - R_{SKIN})/(R_{RMA} - R_{SKIN})$$

where $R_{RMA}$ refers to the reflectance of the RMA. $R_{RMA}$ can be known for the particular RMA used. In the case of $R_{AIM}$, the reflectance corresponds to the desired numerical reflectance. In the case of $R_{SKIN}$ and $R_{RMA}$, the reflectance corresponds to the reflectance of the bulk material (e.g., skin and RMA material, respectively).

The Target Opacity can be translated to an amount of RMA to be applied. In some implementations, and for smaller Target Opacity values, an approximately linear relationship is provided between the Target Opacity and the amount of RMA. For larger Target Opacity values, a relatively non-linear relationship can be provided. In some implementations, the amount of RMA to be applied can be calculated based on the Target Opacity using a pre-defined formula. In some implementations, the amount of RMA to be applied can be determined from a look-up table (e.g., an empirically derived look-up table) using the Target Opacity as an index. The amount of RMA can be provided in units of weight or volume.

In general, color can be described as the reflectance of the skin and/or RMA in a plurality of channels (e.g., red, green and blue). In implementations of the present disclosure, a component of color is used, reflection in green light, for example. Consequently, and in some implementations, $R_{AIM}$, $R_{SKIN}$ and/or $R_{RMA}$ can refer to the reflectance of the aim (i.e., desired, or target), skin and RMA, respectively, in green light. Green is the closest single color approximation of luminance. Luminance is the channel through which the eye is most sensitive to detail, such as seeing defects on skin. Full luminance sensing would require a white light source, which would require up to three times as much light energy to obtain the same signal to noise ratio and overcome ambient light. In some implementations, and to provide for full color corrections, reflectance would be measured for red, green, and blue (RGB) channels. It is appreciated, however, that implementations of the present disclosure are not limited to such. For example, and in a more complex system, there could be three formulas for each color in the tri-stimulus set.

By way of non-limiting example, the following reflectance values can be considered: $R_{SKIN}=50\%$, $R_{AIM}=60\%$, $R_{RMA}=90\%$. Using these example values in the above formula provides:

$$(60-50)/(90-50)=25\%$$

Accordingly, and in the case of lightening of a skin defect, 25% RMA opacity (reflectance) needs to be deposited over the skin to achieve $R_{AIM}$. If, for example, the dots of RMA are each determined to have X % opacity (e.g., 5% opacity) and the calculated amount of RMA to be deposited would result in more than X % opacity, the applicator device 100 should deposit the RMA on the skin in that area. If, however, the calculated amount of RMA to be applied is less than X %, a deposition on that area of an X % opacity dot would over correct the skin (i.e., result in a reflectance that is greater than $R_{AIM}$). If the calculated amount of cosmetic is less than Y % opacity (e.g., 2.5% opacity), deposition would do more damage than good. The decision threshold to deposit may be selected for some percentage between Y % and X % (e.g., 2.5% and 5%). For example, a useful threshold percentage can include 4%.

The formula provided above assumes a linear value of skin reflectance. It has been discovered that the green part of the visible light spectrum is adequate for control to make dark skin defects (e.g., blemishes) bright, for example. Refinements for optically nonlinear RMAs can be accommodated with a more complex formula or more simply by the use of an empirically derived two-dimensional lookup tables.

It is determined whether to apply the calculated amount of RMA to the nominated point (526). For example, the CPU board 124 of the applicator device 100 can determine whether to apply the calculated amount of RMA. In some implementations, and considering a skin defect that is darker than the skin color (i.e., lightening a relatively darker defect), if the calculated amount of the particular RMA exceeds a threshold amount, the RMA is applied to the nominated point (528). The threshold amount may be determined based on the opacity and reflectance of the particular RMA (e.g., pigment) for a layer that can be deposited in a single application. If the calculated amount of the RMA is below the threshold amount, the nominated point of skin is considered to not require treatment.

In some implementations, and considering a skin defect that is lighter than the skin color (i.e., darkening a relatively lighter defect), if the calculated amount of the particular RMA is less than a threshold amount, the RMA is applied to the nominated point (528). The threshold amount may be determined based on the opacity and reflectance of the particular RMA (e.g., dye) for a layer that can be deposited in a single application. If the calculated amount of the RMA is greater than the threshold amount, the nominated point of skin is considered to not require treatment.

It is appreciated that an applicator device in accordance with implementations of the present invention can include a plurality of RMAs that can be applied to the area of skin, the nominated point, in particular. For example, a first RMA can be used to lighten relatively darker defects and a second RMA can be used to darken relatively lighter defects.

As discussed above, the opacity of an RMA deposition is linearly related to the amount of RMA for small amounts of RMA. In the ranges considered here, for example 10% per pulse or less, it may be considered linear for practical purposes. However, ten times the amount of RMA that produces 10% opacity will actually produce approximately 63% opacity, and requires a theoretically infinite amount of cosmetic to achieve absolute 100% opacity. This relationship is provided as an inverse exponential. In some implementations, such as an applicator device employing feedback, the deviation from non-linearity can be ignored if each pass is independently sensed and deposits relatively small amounts of RMA, such as 20% or less opacity per pulse.

The amount of RMA that provides 5% opacity is defined as the amount of RMA necessary to move skin reflectance 5% of the way from untreated skin to the ultimate color of skin, if covered with an infinite amount of RMA.

In some implementations, the example process 500 can include the operation 504. In particular, noise is removed from the image (504). For example, the CPU board 124 of the applicator device 100 can apply a simple median filter to remove impulse and/or electronic noise (e.g., "snow"). The de-noised image can be used for filtering to provide the first filtered image. In general, the effects of any Brownian or electronic noise in the image can be removed from analysis, using techniques such as a median filter over a surrounding area of 1 pixel around the nominated point. In this manner, the single pixels reasonably represent true skin color. This removal of noise can include the removal of detected hairs, as for example with a median filter.

In some implementations, the example process 500 can include the operations 510 and 512. In particular, it is determined whether the image (i.e., the image of operation 502, or the de-noised image of operation 504) is lighter than the first filtered image. If the image is not lighter than the first filtered image, the first filtered image is used as the aim image (514). If the image is lighter than the first filtered image, the image is used as the aim image (512). The lightness of an image can be calculated as a lightness value. The lightness values of two images can be compared, and the image having the highest lightness value can be used as the aim image. By way of non-limiting example, a lightness value can range between 0 and 255. A lightness value of 0 can indicate a completely white image, while a lightness value of 255 can indicate a completely black image.

The refinement provided by operations 510 and 512 ensures that no pixel may be selected that is lighter than the aim color, no matter how dark the surrounding pixels included in the average are. Consequently, the allowed edge of potential correction ends at the edge of a defect independently, and can support the protection described below.

In some implementations, the example process 500 can include the operations 520 and 522. In particular, a minimum reflectance can be determined within a protection area (520). For example, the aim image can be processed by the CPU board 124 of the applicator device 100 to determine the protection area and the minimum reflectance. In general, a randomly selected nominated point is not always centered on a skin defect. Still, the nominated point may be sufficiently close to the skin defect to have a skin color sufficient to drive the deposition of the RMA. If the defect is particularly dark, for example, $R_{SKIN}$ calculated in operation 508 can actually drive a deposition that is centered outside of the skin defect.

This can create several problems. For example, for smaller defects, it may allow an early but mis-aimed deposition that uses up the darkness of the skin defect and prevents a later, possibly better aimed nomination point to properly obscure the skin defect. That is, the skin defect is left with a mis-registered correction point that does not hide the skin defect. Further, darker skin defects may attract several near-miss firings that leave a ring around the skin defect, which rings may not be undone by later, correctly aimed depositions. Further, in a skin area with wide but not very dark skin defects, the correction may occur randomly across the defects rather than start at the peaks of the defect, which may produce an intermediate result on the skin that looks mottled and worse than before the treatment began, but that with further application of RMA, will eventually fill in and look better. All of these cases can be improved by deriving a metric for spatial accuracy of a nominated point relative to the true center of a defect and retarding firing when the accuracy is below a predetermined threshold. The following discussion will show a method of deriving and applying that metric.

A simple way to make the selection more stringent may be to apply a minimum calculation for whether to deposit RMA over a useful protection area. In some implementations, the protection area may be determined by a metric of how close the nominated point is to any other point that requires more correction. This distance should be large enough to provide effective protection from creating a ring around, or partial correction of a defect, but small enough not to suppress correction of proximal but separate defects. In some implementations, a typical value would be approximately the radius of a deposited spot, or in the case above the radius is about half the diameter of a spot used in operation 504. For example, the distance between the nominated point and a point needing more correction than the nominated point is selected to a radius of 0.027". A protection area in a useful shape, the center of which is the point being calculated, may be applied to the calculations in operation 520. In some implementations, a circular shape may be used. In some implementations, other shapes may be used, for example squares. A calculation of a peak reflectance over the protection area may then be made for each point of interest.

A corrected skin reflectance ($R_{SKINCORR}$) is calculated (522). $R_{SKINCORR}$ in operation 522 is provided as the corrected actual skin reflectance at the nominated point that will be used to determine the amount of RMA to be applied (524).

With regard to lightening a darker defect, the reflectance of the darkest point within the protection area may be subtracted from the reflectance of the current nominated point. The reflectance of the darkest point is provided as the peak reflectance for the protection area and, in the case of darkening, it is the minimum reflectance within the protection area. If the nominated point is the darkest point, the output of a simple subtraction is zero, and no protection will be given. However, if a darker point exists within the protection radius, the result of the subtraction is a protection factor that determines the risk of applying the RMA on the nominated point. The protection factor can multiplied by a selected gain "K" to determine how much to suppress deposition. If K is too large, the system will wait for the most accurate nominated points, which may excessively slow deposition. If K is too small, the system may allow inaccurate nominated points to be deposited on. A K of zero effectively turns off the protection function, while a K of infinity effectively forces the requirement of perfect accuracy at the expense of almost infinite time.

With regard to darkening a lighter defect, the reflectance of the lightest point within the protection area may be subtracted from the reflectance of the current nominated point. The reflectance of the lightest point is provided as the peak reflectance for the protection area and, in the case of lightening, it is the maximum reflectance within the protection area. If the nominated point is the lightest point, the output of a simple subtraction is zero, and no protection will be given. However, if a lighter point exists within the protection radius, the result of the subtraction is a protection factor that determines the risk of applying the RMA on the nominated point. Again, the protection factor can multiplied by a selected gain "K" to determine how much to suppress deposition.

In operation 522, the peak reflectance ($R_{PEAK}$) from operation 520 and $R_{SKIN}$ from operation 508 are provided as input and $R_{SKINCORR}$ is provided as output. $R_{SKINCORR}$ is provided as a corrected actual skin reflectance that is subsequently used to determine the amount of RMA to be applied in operation 524. That is, when operations 520 and 522 are implemented, the formula for Target Opacity used in operation 524 is provided as:

Target Opacity (reflectance)=$(R_{AIM}-R_{SKINCORR})/(R_{RMA}-R_{SKINCORR})$ $R_{SKINCORR}$ can be calculated based on the following formula:

$R_{SKINCORR}=R_{SKIN}+K(R_{SKIN}-R_{PEAK})$

K may be empirically selected to provide the needed degree of protection without excessively slowing deposition. Note that, if K=0, $R_{SKINCORR}$ is equal to $R_{SKIN}$, and no correction is provided.

The protection provided in operations 520 and 522 is similar to a sharpening system in that it places light rings around dark defects, or dark rings around light defects as a buffer of protection. By substituting $R_{PEAK}$ with a Gaussian filter, a sharpening filter can be provided. The formula assumes a positive linear imaging system controlling defects. Polarity can be changed to accommodate a negative imaging system. It is also possible to modify the weighting or shape of the protection kernel around each point in computing the peak reflectance just as it is possible to make a sharpening filter with many different kernel shapes, such as a Gaussian shape.

The protection described above could be applied after determining the aim color (operation 518). This can provide a marginally more accurate result. However, the peak reflectance can be used before determining the aim color. In this manner, the median may only need to be calculated at a point known by the processor to be nominated. Typically a median is a computationally expensive operation, and relaxing the requirement to cover only one point or a few points being nominated relieves the processor of some computations.

In some implementations, the processor (e.g., CPU board 124) can be made aware of motion of the handheld device (e.g., the applicator device 100) by means of processing the series of past and present images. In some implementations, the processor can monitor movement of the handheld device based on signals generated by an accelerometer (e.g., accelerometer 122). Using estimators based on momentum, a likely future path including the locus of predicted future nominated points relative to the current image, or current nominated point can be calculated. The processor can review these predicted future nominated points and pick a predicted nominated point and predicted time to apply the RMA that corresponds to a maxima along the line of motion closer to the center of a defect. Functionally, this enables the processor to "aim" by controlling time in the one dimension of movement of the hand.

Implementations of the present disclosure are further directed to RMAs including cosmetics and cosmetic formulations thereof. In particular, RMAs that include pigment-based cosmetic compositions can be used to make cosmetic enhancements using any means of deposition (e.g., spray technology such as airbrushing). For example, these cosmetic enhancements may be to lighten an area, darken an area, and change color values of the area. These pigmented RMAs may be similar to traditional cosmetic formulations, or may deliberately be highly differentiated with respect to desired skin reflectance.

In some implementations, the RMAs may be cosmetic formulations that are designed to be applied in layers, with each layer having the effect of increasing opacity on the skin. For example, cosmetic formulations with very low pigment loads may be used to achieve a smoothing effect on the skin, for example, in the example ranges described in further detail below. The use of a cosmetic formulation with a color that is highly differentiated from the color of the skin to be treated may also be advantageous.

Implementations of the RMA are designed to be used with an applicator that, after each application, measures and compares the reflectance and/or color of the area on which the RMA is applied to those of the surrounding area to determine if the correction threshold has been achieved. For purposes of the present discussion, an RMA drop is the RMA from when it exits the deposition nozzle and is in flight until it contacts the target substrate. The RMA spot is the RMA on the target substrate, such as skin.

The RMA may have a low opacity, so that using an iterative application and feedback method, the optimal level of correction can be achieved without over correcting. Experience and experiments using simulations have shown that an RMA with a 5% opacity, for example, can be used to achieve visually appealing cosmetic treatments within a reasonable amount of time. Using a higher opacity RMA will allow more differentiated skin features to be corrected with fewer applications, which may shorten the time for treatment. A disadvantage of a higher opacity RMA is that the RMA may look heavy on the corrected features and leave less differentiated features untouched, so that the treatment is incomplete. Conversely, using an RMA with very low opacity will allow more precise correction of the skin feature, but will require more applications and time.

The RMA may have a composition that causes it to rapidly adhere to the surface and cure, meaning dry and bind particles, such that successive applications in the same location build in layers without causing previous layers to dissolve. Moreover, the RMA may have a composition such that, when it is wet on the skin, it does not move and, as the volatile carrier evaporates the particulates, such as pigments, form a very thin layer. Ideally, the distribution of the mass of the particulates is Gaussian. An irregular distribution of mass within a circular area of consistent size may also yield acceptable visual results. A distribution of mass concentrated to the parameter of the circle and less in the middle, like a donut or volcano, will not yield visually acceptable results, because the edges will be visually sharp with higher contrast to the surrounding skin. In iterative, multi-layer approaches, such as those described herein, the irregular distribution of the pigment mass within each successive layer unevenly overlaps the first, creating a Gaussian distribution.

The RMA may have a composition that produces circular spots on skin that are approximately $\frac{1}{15}$" (1.7 mm) in diameter when used in one implementation of an applicator. Deposition spots of $\frac{1}{15}$" (1.7 mm) in diameter can be used to achieve visually appealing cosmetic treatments within a reasonable amount of time. Deposition spots smaller than $\frac{1}{15}$" (1.7 mm) in diameter can make an even more appealing result, because skin features smaller than $\frac{1}{15}$" (1.7 mm) in diameter in the middle spatial frequencies can be corrected. A disadvantage of spots smaller than $\frac{1}{15}$" (1.7 mm) in diameter is that the treatment time will be extended. Conversely, using deposition spots larger than 1.7 mm will correct skin features larger than $\frac{1}{15}$" (1.7 mm) in diameter more quickly but leave smaller features untreated, which may create a less appealing result.

The RMA may have a composition such that the reflectance is highly differentiated from skin. Three axes of variability for the RMA are drop landing accuracy, spot shape and consistency, and spot size and consistency. The higher the opacity of the RMA and the more highly differentiated the RMA is from desired skin color, the more accurate and consistent the deposition of RMA should be. Using an RMA that is the same as, or near to, the desired skin tone and that has higher opacity in a less accurate applicator may still yield acceptable visual results on very strong skin features.

The RMA may have a composition that works in the applicator to produce drops of consistent size, shape, viscosity and other physical properties for reliable operation of the applicator. In some implementations, a highly differentiated light cosmetic may be used to correct a dark skin feature and may have particular ranges of characteristics. Example opacity ranges include 1%-40%, 2%-20% and 5%-15%. Example ranges of pigment particle size include 1-30 microns, 1-10 microns and 3-5 microns. The RMA can include a volatile carrier made of a mix of alcohols, water and other ingredients. Example ranges of alcohols in the volatile carrier include 12.0%-68.5% alcohols, 62.0%-68.5% alcohols and 66.6%-67.8% alcohols (e.g., % by weight). An example range for viscosity of the RMA includes 42-44 centipoise (cps).

Implementations of the present disclosure can be used for smoothing the appearance of the skin, skin lightening, simulated natural tanning, and applying shades of color. The application of cosmetics with an apparatus of the present disclosure may also improve the appearance of age spots, rings, veins, bumps, and other skin imperfections as the device is moved over skin. It is not typically necessary for a user to have a high skill level in order to use the deposition device (e.g., the applicator device 100 of FIGS. 1-4).

As discussed above, implementations of the present disclosure include a computerized handheld applicator that can be moved by a user in random directions. In some implementations, the arrangement of the deposition nozzles in a non-linear pattern enables rapid and precise application of one or more RMAs even in view of randomness of direction. In some implementations, three nozzles may be arranged in a triangle within a generally circular pattern. As a result, the user may achieve effective depositions by moving the applicator in random patterns, such as back and forth eraser-like movements, circles, straight lines, zigzags, and wavy lines. This freedom of movement is particularly useful for the iterative application of relatively small amounts of RMA to an area. Such application can be controlled by continual sensing of the area and software calculations of the amount of RMA to be deposited to that area after each sensing to create desired effects. Further, implementations of the present disclosure may use deposition nozzles, where each nozzle fires, or otherwise applies an RMA independently when a detected target, or nominated point on the skin is beneath the particular nozzle.

As also discussed above, implementations of the present disclosure may use software methods on the computerized applicator that enable rapid and precise processing to create desired effects. In some implementations, this can be achieved through the random and typically iterative movement of the applicator over the skin. Examples of these software methods may include the use of a method for the prevention of undesirable deposition on the edges of defects. Further, implementations of the present disclosure provide for a rapid median average for calculating a target, or aim reflectance. The rapid median average can be performed only over the pixels surrounding a specific point to be treated, and only for the single pixel centered over the area immediately below a deposition nozzle, for example.

As also discussed above, implementations of the present disclosure provide for the use of RMA formulations that are designed to be applied iteratively in layers, with each layer having the effect of increasing opacity on the skin. For example, cosmetic formulations with very low pigment loads may be used to achieve a smoothing effect on the skin, much lower pigment loads than has typically been possible with previous cosmetics. The low pigment load further enables the computerized applicator to create opacity in the deposition, so that repeated applications of relatively small amounts of RMA onto the same area can be used to create subtle desired effects. The application of RMA formulations in layers and with low pigment loads also enables the use of RMAs that are highly differentiated in luminance relative to the luminance of the skin to be treated.

The features described can be implemented in digital electronic circuitry, or in computer hardware, firmware, software, or in combinations of them. The apparatus can be implemented in a computer program product tangibly embodied in an information carrier, e.g., in a machine-readable storage device, for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. Elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other implementations are within the scope of the following claims.

A number of implementations of the present disclosure have been described. Nevertheless, it will be understood that various modifications may be made without departing from the spirit and scope of the present disclosure. Accordingly, other implementations are within the scope of the following claims.

What is claimed is:

1. A computer-implemented method for selectively applying a reflectance modifying agent (RMA) to an area of skin, the method comprising:
   receiving an image of the area of skin;
   generating a filtered image based on the image;
   comparing the filtered image to the image;
   determining that the image is lighter than the filtered image based on the comparing;
      identifying, using the filtered image, a nominated point within the area of skin;
   determining an actual reflectance of the nominated point;
   applying an edge protection technique based on the filtered image to generate one or more outputs;

determining a desired reflectance of the nominated point based on the one or more outputs;

calculating an amount of RMA to be applied based on the output; and determining whether to apply the RMA to the area of skin based on the amount of RMA.

2. The method of claim 1, further comprising: determining that the filtered image is lighter than the image based on the comparing; and providing the filtered image as the output.

3. The method of claim 1, wherein applying an edge protection technique comprises:

defining a protection area that is larger than the nominated point and that encompasses the nominated point;

identifying a peak reflectance within the protection area; and generating an output of the one or more outputs based on the peak reflectance and the actual reflectance.

4. The method of claim 3, wherein the output comprises a corrected actual reflectance.

5. The method of claim 4, wherein the corrected actual reflectance is calculated based on the following equation:

$$R_{SKINCORR} = R_{SKIN} + K(R_{SKIN} - R_{PEAK})$$

where $R_{SKINCORR}$ is the corrected actual reflectance, $R_{SKIN}$ is the actual reflectance, $R_{PEAK}$ is the peak reflectance and K is a gain.

6. The method of claim 3, wherein the peak reflectance is a minimum reflectance.

7. The method of claim 3, wherein the peak reflectance is a maximum reflectance.

8. The method of claim 1, further comprising calculating a target opacity based on the desired reflectance, the output and a reflectance of the RMA, wherein the amount of RMA is determined based on the target opacity.

9. The method of claim 8, wherein the amount of RMA is determined from a look-up table using the target opacity as an input.

10. A handheld device for selectively applying a reflectance modifying agent (RMA) to an area of skin, the device comprising:

at least one image generator; and one or more processors that are in communication with the at least one image generator and that are operable to perform operations comprising:

receiving an image of the area of skin;

generating a filtered image based on the image;

comparing the filtered image to the image;

determining that the image is lighter than the filtered image based on the comparing;

identifying, using the filtered image, a nominated point within the area of skin;

determining an actual reflectance of the nominated point;

applying an edge protection technique based on the filtered image to generate one or more outputs;

determining a desired reflectance of the nominated point based on the one or more outputs;

calculating an amount of RMA to be applied based on the output; and determining whether to apply the RMA to the area of skin based on the amount of RMA.

11. The handheld device of claim 10, wherein the device is guided over the area of skin in a random motion.

12. The handheld device of claim 10, wherein the device further comprises:

one or more deposition nozzles; and a cartridge that contains the RMA and that is in fluid communication with at least one of the one or more deposition nozzles.

13. The handheld device of claim 12, wherein the one or more deposition nozzles are arranged in a non-linear pattern.

14. The handheld device of claim 12, wherein each deposition nozzle of the one or more deposition nozzles is independently operable to deposit an RMA.

15. The handheld device of claim 10, further comprising at least one illuminator.

16. The handheld device of claim 10, further comprising a polarizing filter.

17. The handheld device of claim 10, further comprising an illumination dome.

18. A non-transitory computer-readable storage medium coupled to one or more processors and having instructions stored thereon which, when executed by the one or more processors, cause the one or more processors to perform operations for selectively applying a reflectance modifying agent (RMA) to an area of skin, the operations comprising:

receiving an image of the area of skin;

generating a filtered image based on the image;

comparing the filtered image to the image;

determining that the image is lighter than the filtered image based on the comparing;

identifying, using the filtered image, a nominated point within the area of skin;

determining an actual reflectance of the nominated point;

applying an edge protection technique based on the filtered image to generate one or more outputs;

determining a desired reflectance of the nominated point based on the one or more outputs;

calculating an amount of RMA to be applied based on the output; and determining whether to apply the RMA to the area of skin based on the amount of RMA.

* * * * *